(12) United States Patent
McMillan et al.

(10) Patent No.: US 8,277,460 B2
(45) Date of Patent: Oct. 2, 2012

(54) IMPACTOR

(75) Inventors: Iain Alexander McMillan, Christchurch (NZ); Paul John Morrison, Christchurch (NZ)

(73) Assignee: Enztec Limited (NZ)

( * ) Notice: Subject to any disclaimer, the term of this patent is extended or adjusted under 35 U.S.C. 154(b) by 777 days.

(21) Appl. No.: 12/374,796

(22) PCT Filed: Aug. 1, 2007

(86) PCT No.: PCT/NZ2007/000200
§ 371 (c)(1),
(2), (4) Date: Jan. 23, 2009

(87) PCT Pub. No.: WO2008/016312
PCT Pub. Date: Feb. 7, 2008

(65) Prior Publication Data
US 2009/0312766 A1    Dec. 17, 2009

(30) Foreign Application Priority Data
Aug. 1, 2006 (NZ) ......................... 548878

(51) Int. Cl.
*A61B 17/58* (2006.01)
(52) U.S. Cl. ......................................................... 606/99
(58) Field of Classification Search ................ 606/86 A, 606/86 R, 87, 88, 91, 99, 100; 623/18.11
See application file for complete search history.

(56) References Cited

U.S. PATENT DOCUMENTS

| 5,951,564 | A * | 9/1999 | Schroder et al. | 606/100 |
| 2004/0122437 | A1 * | 6/2004 | Dwyer et al. | 606/87 |
| 2005/0015094 | A1 | 1/2005 | Keller | |
| 2005/0209597 | A1 * | 9/2005 | Long et al. | 606/86 |
| 2006/0030860 | A1 | 2/2006 | Peterman | |

FOREIGN PATENT DOCUMENTS
DE       20 2005 01427       1/2007

* cited by examiner

*Primary Examiner* — Kevin T Truong
*Assistant Examiner* — Diana S Jones
(74) *Attorney, Agent, or Firm* — Galbreath Law Offices, P.C.; John A. Galbreath

(57) ABSTRACT

An impactor for positioning and holding a surgical or veterinary prosthetic implant while it is being driven into position, said impactor including:
(a) an impaction means;
(b) an impaction shoe which is configured to receive and support a prosthetic implant in a predetermined position;
(c) connection means which connect the impaction means to the impaction shoe and are configured to transmit an impact from the impaction means to the impaction shoe;
(d) arms configured to engage an implant supported upon the impaction shoe;
(e) said arms being biased into engagement with said implant, but movable against the bias out of engagement with the implant;
(f) said connection means being adjustable between a first setting at which the impaction shoe is spring-loaded so as to bias an implant supported upon the impaction shoe into engagement with said arms but at which the impaction shoe can slide relative to said arms, against said spring bias; and a second setting at which both the impaction shoe and the arms are rigidly engaged with an implant supported upon the impaction shoe, to hold the implant in a predetermined position and orientation relative to the impaction means.

5 Claims, 5 Drawing Sheets

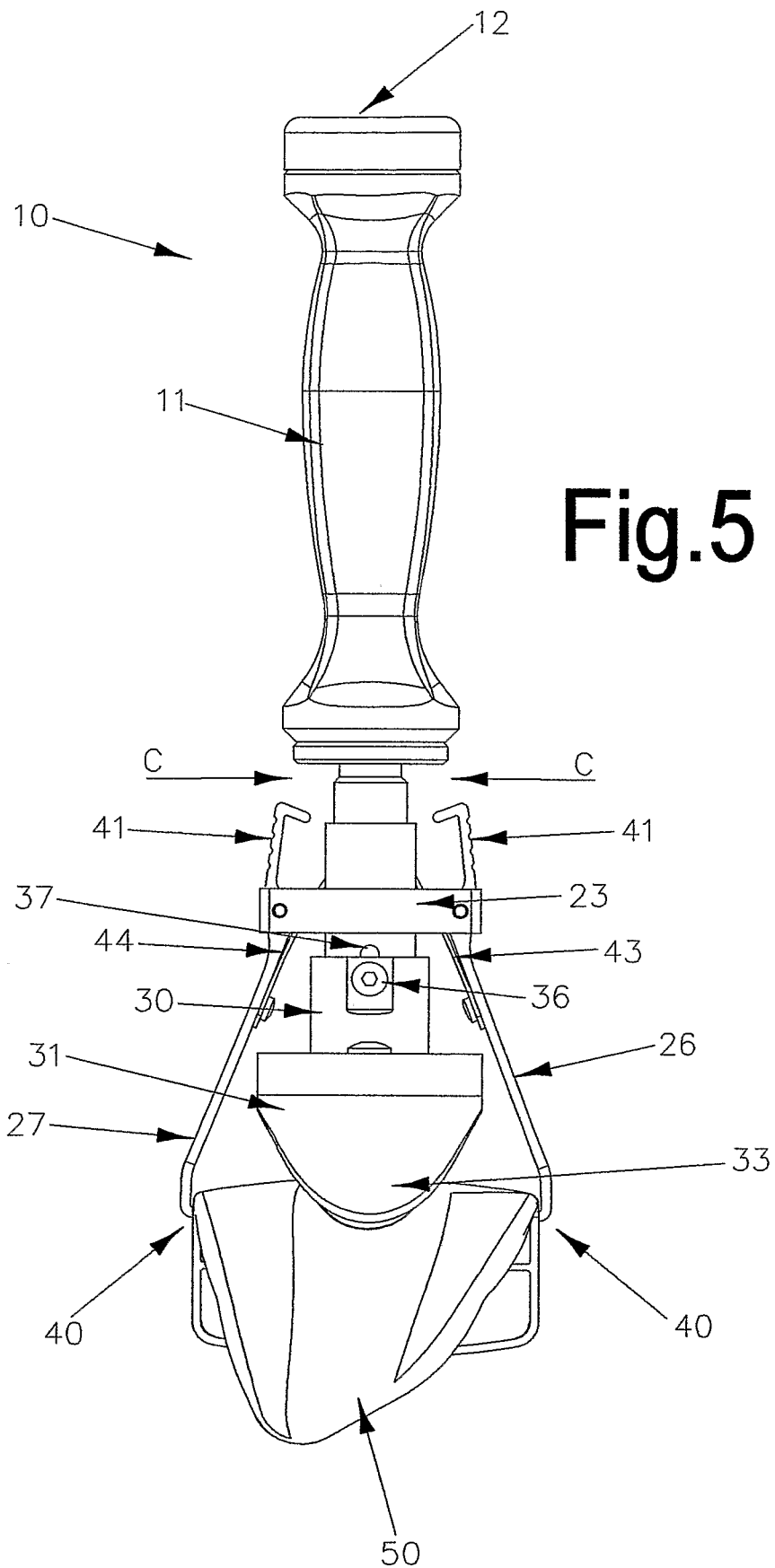

IMPACTOR

BACKGROUND OF THE INVENTION (1) Field of the Invention

The present invention relates to an impactor for positioning and holding surgical or veterinary prosthetic implants while they are being driven into position. The present invention has been designed specifically for femoral knee implants, and therefore will be described with particular reference to that application. However, it will be appreciated that the impactor of the present invention could be adapted for use with any surgical or veterinary prosthetic implant which requires driving into position.

(2) Description of Related Art

Any discussion of the prior art is not an admission that such prior art is widely known or forms part of the common general knowledge in the field.

Ideally, an impactor needs to be capable of holding a range of different sizes of implants, and must also be capable of holding each implant in the correct orientation during impact.

Some of the known impactors are designed specifically for a particular design of implant: for example, the impactors disclosed in U.S. Pat. Nos. 5,951,564, 6,063,124 and 5,059,196.

It is a significant advantage if an impactor is easy to manipulate when the implant is being fitted on the impactor, since the implant is sterile and it is important that handling is minimized. However, known designs of impactor typically require very precise, positive adjustment to engage the impactor correctly with the implant, and this is not always easy to achieve under surgical conditions. The impactor disclosed in U.S. Pat. No. 5,417,693 does allow a small amount of play between the impactor and the implant before final clamping, but only in a plane perpendicular to the axis of the impactor.

BRIEF SUMMARY OF THE INVENTION

An object of the present invention is the provision of an impactor which is capable of holding an implant in the correct orientation during impact, but which can be quickly and easily engaged with an implant.

The present invention provides an impactor for positioning and holding a surgical or veterinary prosthetic implant while whilst it is being driven into position, said impactor including:
(a) an impaction means;
(b) an impaction shoe which is configured to receive and support a prosthetic implant in a predetermined position;
(c) connection means which connect the impaction means to the impaction shoe and are configured to transmit an impact from the impaction means to the impaction shoe;
(d) arms configured to engage an implant supported upon the impaction shoe;
(e) said arms being biased into engagement with said implant, but movable against the bias out of engagement with the implant;
(f) said connection means being adjustable between a first setting at which the impaction shoe is spring-loaded so as to bias an implant supported upon the impaction shoe into engagement with said arms but at which the impaction shoe can slide relative to said arms, against said spring bias; and a second setting at which both the impaction shoe and the arms are rigidly engaged with an implant supported upon the impaction shoe, to hold the implant in a predetermined position and orientation relative to the impaction means.

Preferably, the connection means includes an impactor plate which is rigidly connected to one end of a shaft, the other end of which is configured to be in load transmitting engagement with the impaction shoe when said impaction shoe is at said second setting.

The present invention further provides an impactor for positioning and holding a surgical or veterinary prosthetic implant whilst it is being driven into position, said impactor including:
(a) an impaction means which includes a handle having a longitudinal axis along which impact is transmitted in use;
(b) an impaction shoe which is configured to receive and support a prosthetic implant in a predetermined position;
(c) connection means which provide an impact-transmitting connection between the impaction means and the impaction shoe;
(d) arms configured to engage an implant supported upon the impaction shoe, said arms being biased into engagement with said implant, but movable against the bias out of engagement with the implant;
(e) said connection means being adjustable between a first setting at which the impaction shoe is spring-loaded so as to bias an implant supported upon the impaction shoe into engagement with said arms but at which the impaction shoe can slide relative to said arms, against said spring bias; and a second setting at which both the impaction shoe and the arms are rigidly engaged with an implant supported upon the impaction shoe, to hold the implant in a predetermined position and orientation relative to the impaction means;
(f) said connection means including a shaft having a longitudinal axis aligned with the longitudinal axis of the handle, one end of the said shaft carrying an impactor plate which is configured to be in load transmitting engagement with said handle, and the other end of said shaft being configured to be in load transmitting engagement with the impaction shoe when said impaction shoe is at said second setting.

Preferably, a portion of said shaft is externally screw threaded and is in screw threaded engagement with a housing which is slideably engaged with the impaction shoe; said impactor further including a spring mounted between the impaction shoe and the housing, said spring being configured to bias the impaction shoe away from the housing; said shaft and said housing being configured such that when said connection means is at said first setting, said screw threaded portion of said shaft is only partially engaged with the housing, and when said connection means is at said second setting, said screw threaded portion of said shaft is fully engaged with the housing and said other end of said shaft is in load transmitting engagement with the impaction shoe.

The present invention also provides an impactor component for use in combination with an impaction means, said impactor component including:
(a) an impaction shoe which is configured to receive and support a prosthetic implant in a predetermined position;
(b) connection means which are configured to connect the impaction means to the impaction shoe and to transmit an impact from the impaction means to the impaction shoe;
c) arms configured to engage an implant supported upon the impaction shoe, said arms being biased into engagement with said implant, but movable against the buyers out of engagement with the implant;
(d) said connection means being adjustable between a first setting at which the impaction shoe is spring-loaded so as to bias an implant supported upon the impaction shoe into engagement with said arms but at which the impaction shoe can slide relative to said arms, against said spring bias; and a second setting at which both the impaction shoe and the arms are rigidly engaged with an implant supported upon the impaction shoe, to hold the implant in a predetermined position and orientation relative to the impaction means.

The impaction means may be any suitable means e.g. a handle with an anvil at one end which can be struck by a suitable tool, or a slap hammer, or a combined multi-purpose handle.

As used herein the term 'implant' includes part of an implant.

BRIEF DESCRIPTION OF THE DRAWINGS

By way of example only, a preferred embodiment of the present invention is described in detail, with reference to the accompanying drawings, in which:

FIG. 5 is an isometric view of the impactor with an implant in place.

DETAILED DESCRIPTION OF THE INVENTION

Figure 1:
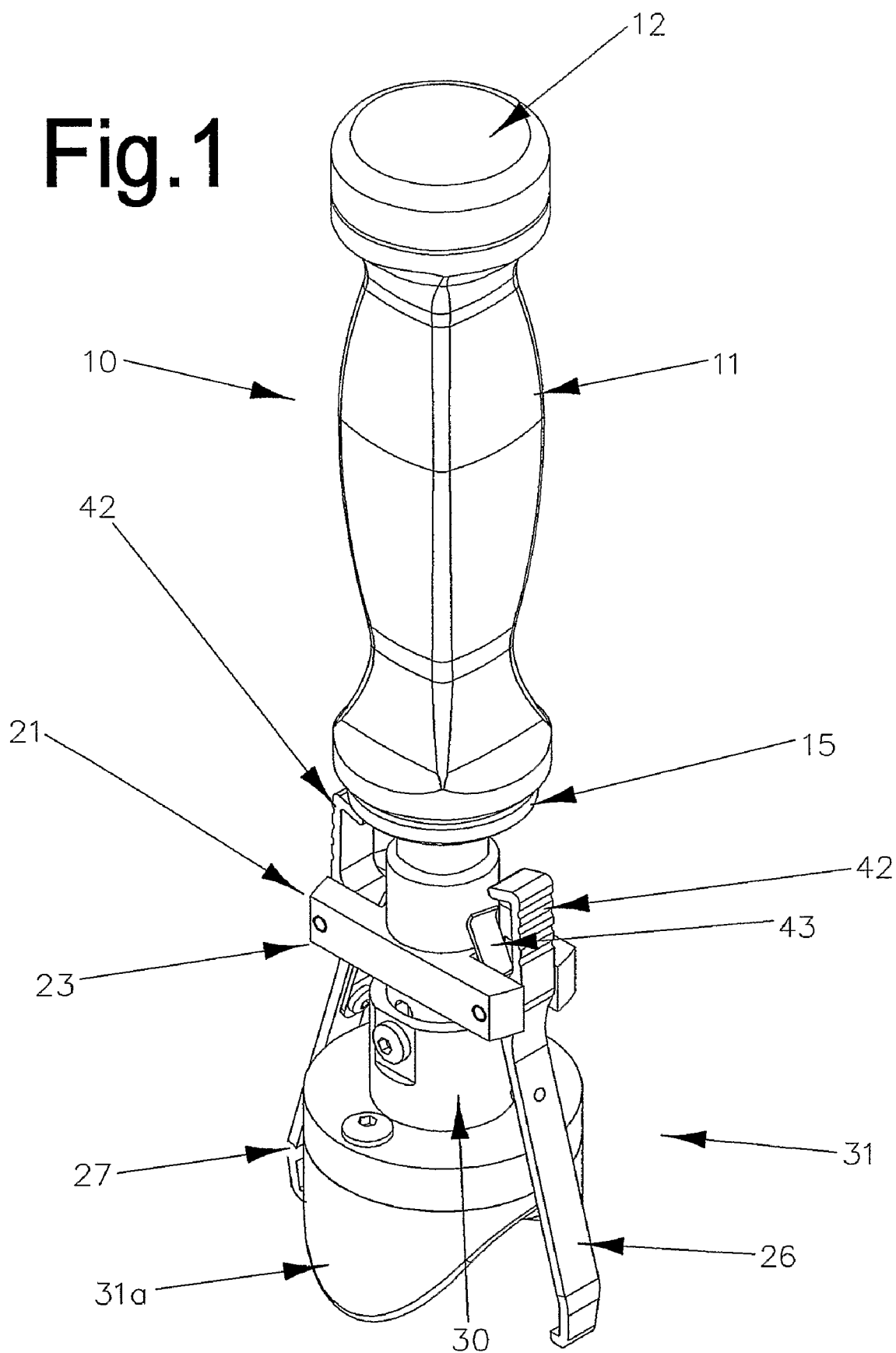
FIG. 1 is an isometric view of an impactor in accordance with the present invention.

Referring to the drawings, an impactor 10 in accordance with the present invention includes an impaction means in the form of a handle 11 which carries an anvil 12 at one end. The anvil 12 may be formed integrally with the top of the handle. The handle 11 is connected to an impaction shoe 31 by connection means which include shafts 13 and 16 and housing 21.

The other end of the handle 11 is mounted upon a first shaft 13 which extends along part of the longitudinal axis of the handle 11. The shaft 13 is formed integrally with an impact plate 15 in contact with the other end of the handle. The side of the impact plate 15 opposite to the shaft 13 is formed integrally with a second shaft 16 coaxial with the shaft 13. The portion 17 of the second shaft 16 adjacent to the impact plate 15 is externally screw threaded; the remaining portion of the shaft 16 is of reduced diameter and formed as a smooth cylinder 18. A coil spring 19 is mounted upon the cylinder 18.

The portion 17 of the shaft 16 is in screw threaded engagement with one end 20 of the interior bore of a housing 21, which is formed with a complimentary screw-thread. The other end 22 of the housing provides an open ended hollow cylindrical portion which houses the spring 19. The housing 21 carries a bracket 23 which provides pivotal mountings for two opposed arms 26,27.

The end 22 of the housing 21 is an easy sliding fit within a cylindrical boss 30 formed on one side of an impaction shoe 31. The spring 19 is held between the end 22 of the housing within the boss 30 and the adjacent end 32 of the boss 30; the spring surrounds the cylinder 18.

The other side 31a of the impaction shoe 31 is formed as a pair of diverging shoulders 33, with a U-shaped hollow 34 between the shoulders. The size and shape of the side 31a of the shoe 31 is designed to receive known designs of femoral implants, and to positively locate with the implant so that the implant is kept not only in place on the impaction shoe, but in the correct orientation, during impaction. It will be appreciated that the size and shape of the side 31a may be varied as necessary to suit the particular size, shape, and type of the implant.

Figure 3:
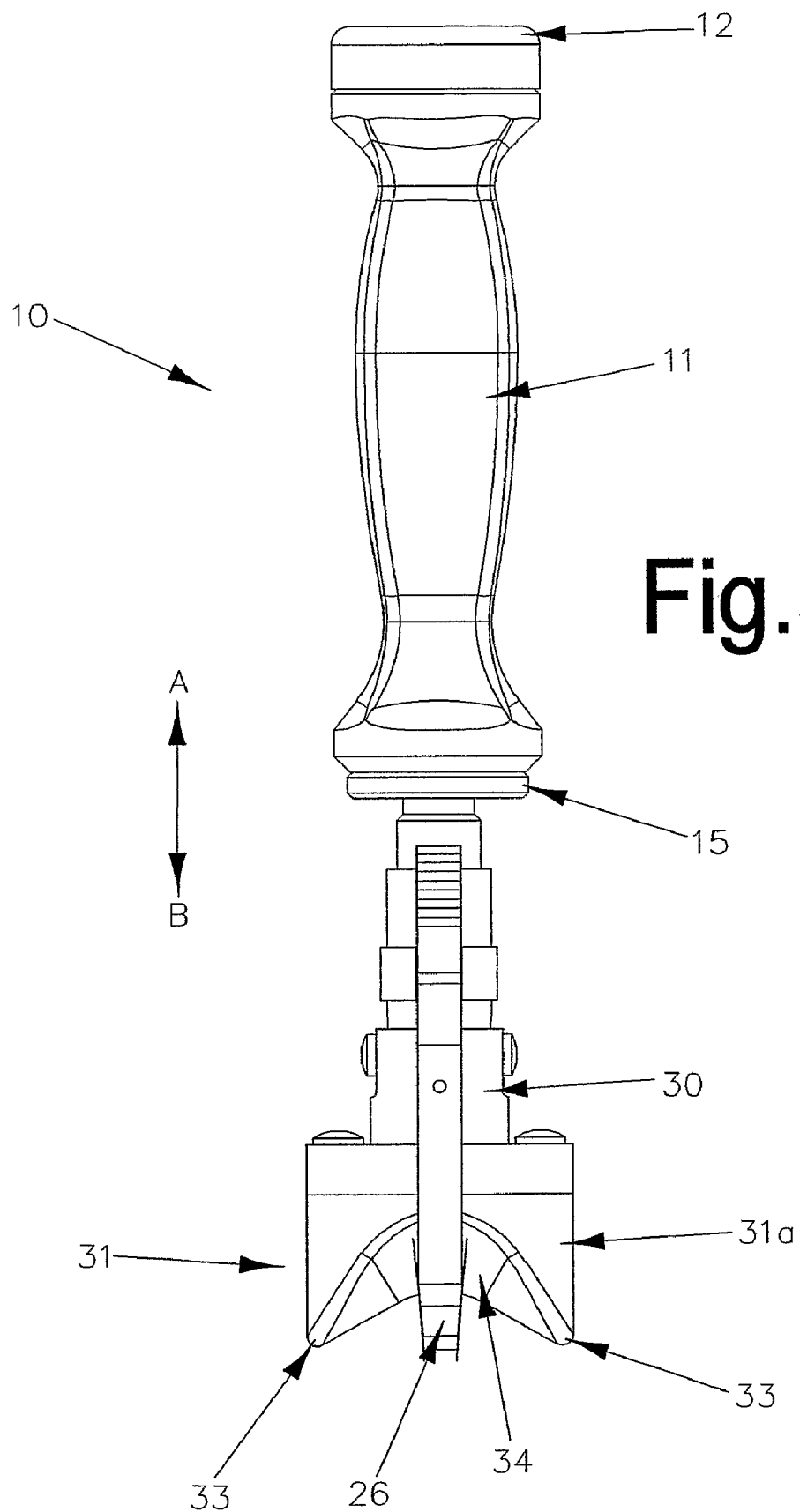
FIG. 3 is a side view at 90° to the view of FIG. 2 on a larger scale.
Figure 4:
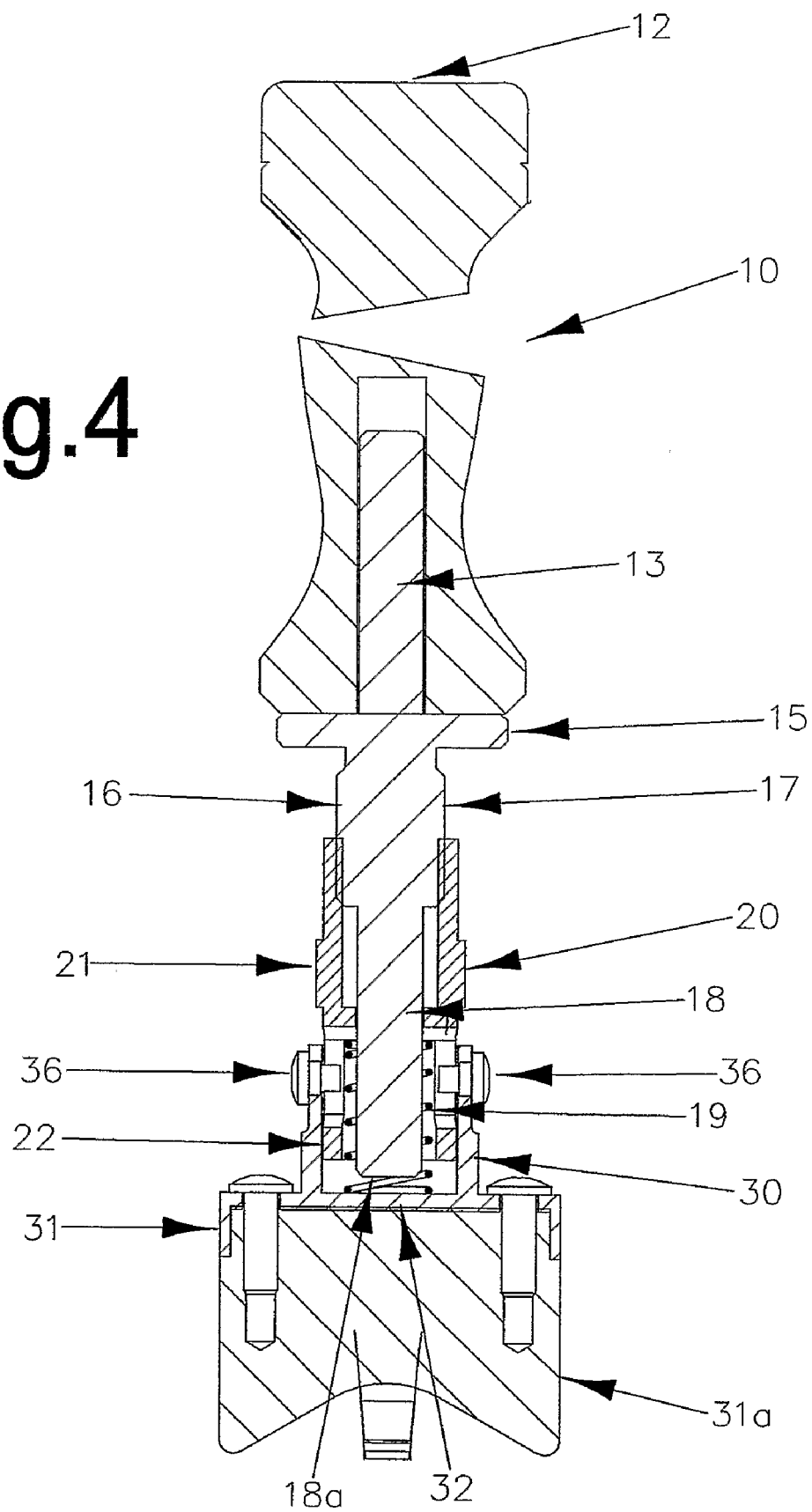
FIG. 4 is a section on line A-A of FIG. 2 on a larger scale.

The boss 30 is slidably secured to the end 22 of the housing by means of a pair of opposed pins 36, each of which passes through a hole in the boss 32 to engage a slot 37 which extends along opposed sides of the end 22, parallel to the longitudinal axis of the housing. This arrangement allows limited movement of the impaction shoe 31 in the directions of arrows A and B (FIG. 3), but maintains the orientation of the impaction shoe 31 relative to the remainder of the tool.

Each of the arms 26,27 has a portion 39 which extends forwards from the bracket 23, ending in a hooked portion 40 which lies in a plane slightly below the plane of the shoulders 33 of the impaction shoe 31.

Figure 2:
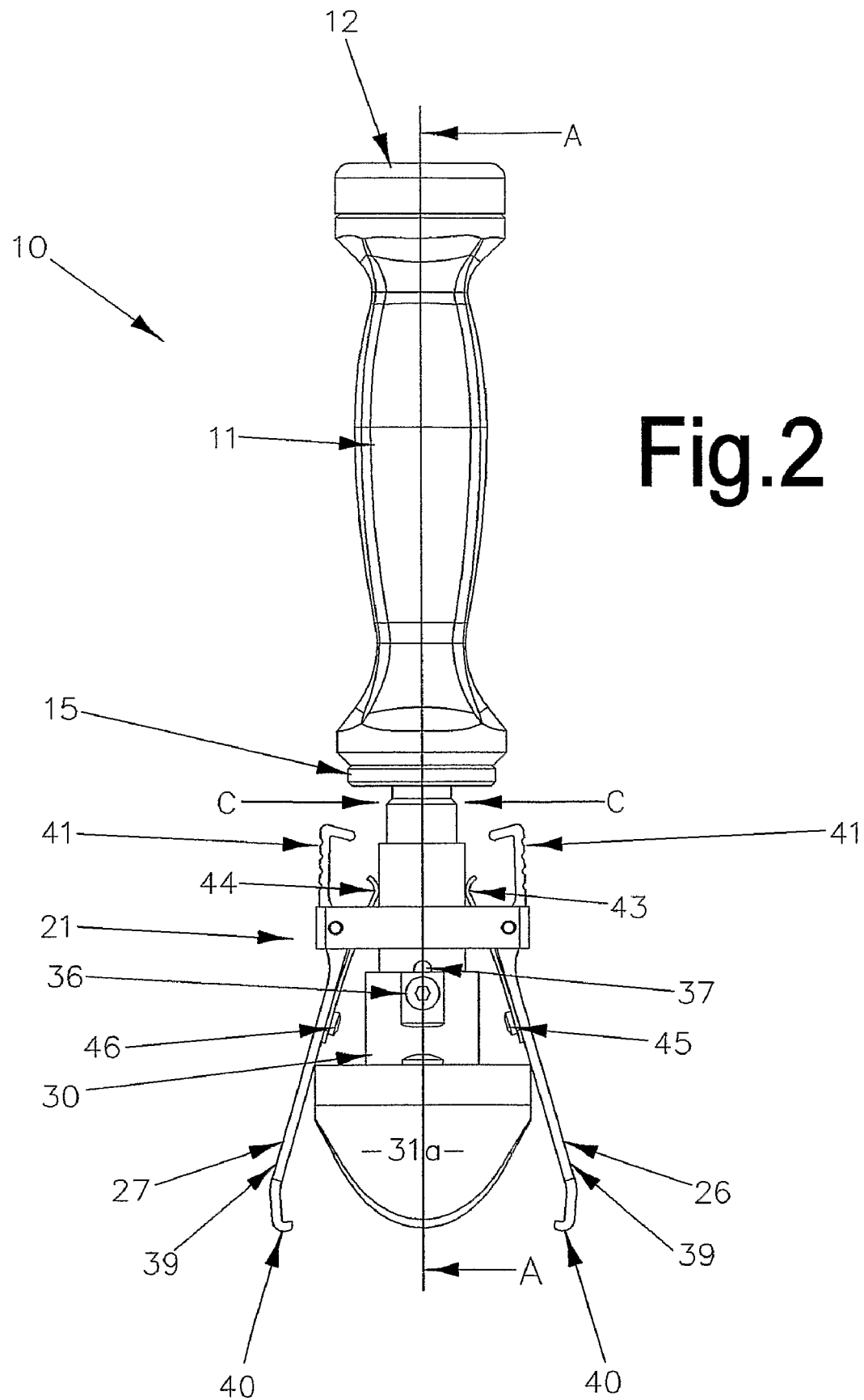
FIG. 2 is a side view of the impactor of FIG. 1.

Each of the arms 26,27 also has a portion 41 which lies on the handle side of the bracket 23 and is textured on its outer surface 42 to allow the arms to be easily and positively gripped. A leaf spring 43, 44 is secured to the corresponding arm 26,27 by a rivet 45,46; each leaf spring 43,44 bears against the outer surface of the housing at its inner end, so as to bias the portions 41 of the arms apart and the hooked ends 40 together. This bias may be overcome by manually pressing the portions 41 of the arms towards the housing i.e. in the directions of arrows C (FIG. 2).

Alternatively, the leaf springs 43,44 may be formed integrally with the corresponding arms 26,27. Other types of resiliently biasing of the arms 26,27, may be substituted, e.g. pads of resilient material.

The above described impactor is used as follows: first, the handle 11 is rotated to move the lower end 18a of the cylinder 18 away from the end 32 of the boss 30. The screw thread formed on the portion 17 of the shaft 16 is reasonably long (typically 20 mm), so that the end 18a can move several millimetres away from the end 32 of the boss 30 without the handle 11 becoming disengaged from the housing 21. In this position, the boss 30 and shoe 31 can slide relative to the housing 21 in the directions of arrows A and B.

An implant 50 (shown only in FIG. 5) is then mounted upon the impaction shoe 31 by pressing the portions 41 of the arms 26,27 in the direction of arrows C, and pressing the implant over the impaction shoe 31 such that the implant is positively located on the impaction shoe with one of the shoulders 33 on each side of the implant, so that the implant cannot rotate relative to the impaction shoe. The portions 41 are then released so that the leaf springs 43,44 bias the arms 26,27 towards the impaction shoe and the hooked ends 40 of the arms engage the implant 50 to hold the implant firmly and positively in position on the impaction shoe. The implant 50 may be formed with indentations to receive the ends 40.

It will be appreciated that the spring 19 allows the position of the impaction shoe 31 relative to the arms 26,27 to be adjusted easily, with minimal handling of the implant 50, to ensure that the hooked ends 40 make a proper engagement with the implant 50. Once the implant is in position, the bias of the spring 19 against the impaction shoe 31 results in the implant being pressed against the ends 40 of the arms 26,27, maintaining the implant in position relative to the impactor. However, before the implant is driven into place, it is necessary to remove the play allowed by the spring 19, and to do this the handle 11 is rotated to screw the portion 17 of the second shaft 16 into the end 20 of the housing 21, until the end 18a of the cylinder 18 contacts the inner end 32 of the boss, so that any impact on the anvil 12 is transmitted directly to the impaction shoe 31. In this position, the hooked ends 40 are pulled into tight engagement with the implant, thus pulling the implant into a firm engagement with the impaction shoe 31. This "tightening" can be done without handling the implant 50 at all.

It will be appreciated that the implant 50 is sterile, and must be kept so until fitted to the patient. However, it is very important to the success of the operation that the implant 50 is correctly engaged with the impaction shoe and thus is correctly oriented for being driven into position. The impactor of the present invention allows the position of the impaction shoe to be adjusted relative to the arms, quickly and easily, and thus facilitates the correct positioning of the implant 50, without the need to touch the implant. Once the implant is correctly positioned, the impactor can be quickly and easily tightened up for driving, again without touching the implant 50.

The anvil 12 is then impacted in known manner to drive the implant into position. During driving, it is necessary only to hold the handle in the desired orientation: the remainder of the impactor cannot rotate relative to the handle nor can the implant move relative to the impaction shoe. When the implant has been driven into position, the handle 11 is rotated in the opposite direction relative to the housing 21, to allow the impaction shoe 31 to slide relative to the housing, and the portions 41 of the arms 26,27 are pressed in the direction of arrows C to release the hooked ends 40 from engagement with the implant. The impactor can then be removed.

It is envisaged that in the above described impactor, the handle 11 and anvil 12 could be replaced by a slap hammer. However, if a slap hammer is used, the sliding weight of the hammer and the shaft along which the hammer slides both are formed with flats so that as the weight slides along the shaft, the impactor does not rotate. An impactor incorporating a slap hammer also can be used to remove prosthesis components.

Another possibility is to use a proprietary handle which can function either as an anvil or as a slap hammer. A further possibility is to replace the impact plate 15 and handle 11 by a coupling which allows a modular handle or a modular slap hammer or a modular combination handle/slap hammer to be attached: this feature would be used if customers wished to use their existing designs of modular handles with the device of the present invention.

The above described impactor is made of fully sterilisable materials.

The invention claimed is:

1. An impactor for positioning and holding a surgical or veterinary prosthetic implant while it is being driven into position, said impactor including:
   (a) an impaction means;
   (b) an impaction shoe which is configured to receive and support a prosthetic implant in a predetermined position;
   (c) connection means which connect the impaction means to the impaction shoe and are configured to transmit an impact from the impaction means to the impaction shoe;
   (d) arms configured to engage an implant supported upon the impaction shoe;
   (e) each of said arms being spring biased by a first biasing means into engagement with said implant, wherein each of said arms is movable against the bias of said first biasing means out of engagement with the implant;
   (f) said connection means being adjustable between a first setting at which the impaction shoe is spring-loaded by a second biasing means so as to spring bias an implant supported upon the impaction shoe into engagement with said arms but at which the impaction shoe can slide relative to said arms, against said spring bias of said second biasing means; and a second setting at which both the impaction shoe and the arms are rigidly engaged with an implant supported upon the impaction shoe, to hold the implant in a predetermined position and orientation relative to the impaction means;
   (g) wherein the connection means includes an impactor plate which is rigidly connected to one end of a shaft, the other end of which is configured to be in load transmitting engagement with the impaction shoe when said connection means is at said second setting;
   (h) wherein a portion of said shaft is externally screw threaded and is in screw threaded engagement with a housing which is slidably engaged with the impaction shoe; said second biasing means comprising a spring mounted between the impaction shoe and the housing, said spring being configured to bias the impaction shoe away from the housing;
   (i) said shaft and said housing being configured such that when said connection means is at said first setting said screw threaded portion of said shaft is only partially engaged with the housing and when said connection means is at said second setting, said screw threaded portion of said shaft is fully engaged with the housing and said other end of said shaft is in load transmitting engagement with the impaction shoe.

2. The impactor as claimed in claim 1 wherein the impaction means is selected from the group consisting of: a handle fitted with an anvil at one end, a slap hammer incorporating a handle, a combined multipurpose handle which provides both an anvil and a slap hammer.

3. The impactor as claimed in claim 1 or claim 2, wherein said spring comprises a coil spring arranged around said other end of said shaft.

4. An impactor for positioning and holding a surgical or veterinary prosthetic implant while it is being driven into position, said impactor including:
   (a) an impaction means which includes a handle having a longitudinal axis along which impact is transmitted in use;
   (b) an impaction shoe which is configured to receive and support a prosthetic implant in a predetermined position;
   (c) connection means which provide an impact-transmitting connection between the impaction means and the impaction shoe;
   (d) arms configured to engage an implant supported upon the impaction shoe, each of said arms being spring biased by a first biasing means into engagement with said implant, wherein each of said arms is movable against the bias of said first biasing means out of engagement with the implant;
   (e) said connection means being adjustable between a first setting at which the impaction shoe is spring-loaded by a second biasing means so as to spring bias an implant supported upon the impaction shoe into engagement with said arms but at which the impaction shoe can slide relative to said arms, against said spring bias of said second biasing means; and a second setting at which both the impaction shoe and the arms are rigidly engaged with an implant supported upon the impaction shoe, to hold the implant in a predetermined position and orientation relative to the impaction means;
   (f) said connection means including a shaft having a longitudinal axis aligned with the longitudinal axis of the handle, one end of the said shaft carrying an impactor plate which is configured to be in load transmitting engagement with said handle, and the other end of said shaft being configured to be in load transmitting engagement with the impaction shoe when said connection means is at said second setting;
   (g) wherein a portion of said shaft is externally screw threaded and is in screw threaded engagement with a housing which is slidably engaged with the impaction shoe; said second biasing means comprising a spring mounted between the impaction shoe and the housing, said spring being configured to bias the impaction shoe away from the housing; and (h) said shaft and said housing being configured such that when said connection means is at said first setting, said screw threaded portion of said shaft is only partially engaged with the housing, and when said connection means is at said second setting, said screw threaded portion of said shaft is fully engaged with the housing and said other end of said shaft is in load transmitting engagement with the impaction shoe.

5. An impactor component for use in combination with an impaction means, said impactor component including:

(a) an impaction shoe which is configured to receive and support a prosthetic implant in a predetermined position;

(b) connection means which are configured to connect the impaction means to the impaction shoe and to transmit an impact from the impaction means to the impaction shoe;

(c) arms configured to engage an implant supported upon the impaction shoe, each of said arms being spring biased by a first biasing means into engagement with said implant, wherein each of said arms is movable against the bias of said first biasing means out of engagement with the implant;

(d) said connection means being adjustable between a first setting at which the impaction shoe is spring-loaded by a second biasing means so as to spring bias an implant supported upon the impaction shoe into engagement with said arms but at which the impaction shoe can slide relative to said arms, against said spring bias of said second biasing means; and a second setting at which both the impaction shoe and the arms are rigidly engaged with an implant supported upon the impaction shoe, to hold the implant in a predetermined position and orientation relative to the impaction means;

(e) wherein the connection means includes a shaft, one end of which is configured to connect to an impaction means and the other end of which is configured to be in load transmitting engagement with the impaction shoe when said connection means is at said second setting;

(f) wherein a portion of said shaft is externally screwed threaded and is in screw threaded engagement with a housing which is slidably engaged with the impaction shoe; said second biasing means comprising a spring mounted between the impaction shoe and the housing, said spring being configured to bias the impaction shoe away from the housing; and (g) said shaft and said housing being configured such that when said connection means is at the first setting, said screw threaded portion of said shaft is only partially engaged with the housing, and when said connection means is at said second setting, said screw threaded portion of said shaft is fully engaged with the housing and said other end of said shaft is in load transmitting engagement with the impaction shoe.

* * * * *